United States Patent
Agisim et al.

(10) Patent No.: US 9,427,416 B2
(45) Date of Patent: Aug. 30, 2016

(54) COMPOSITION AND METHOD FOR TREATING HEMORRHOIDS AND/OR ANORECTAL DISORDERS

(75) Inventors: Gary Robert Agisim, Henrico, VA (US); Richard John Kenny, Glen Allen, VA (US); Miron Gerard Still, Richmond, VA (US); Ellen Bland Gilliam, Hopewell, VA (US); Helen Elizabeth Taylor, Richmond, VA (US)

(73) Assignee: Wyeth LLC, New York, NY (US)

( * ) Notice: Subject to any disclaimer, the term of this patent is extended or adjusted under 35 U.S.C. 154(b) by 0 days.

(21) Appl. No.: 13/537,473

(22) Filed: Jun. 29, 2012

(65) Prior Publication Data

US 2012/0264757 A1    Oct. 18, 2012

Related U.S. Application Data

(60) Continuation of application No. 12/614,084, filed on Nov. 6, 2009, now abandoned, which is a division of application No. 10/884,464, filed on Jul. 2, 2004, now abandoned.

(51) Int. Cl.
*A61K 31/137*    (2006.01)
*A61K 31/24*    (2006.01)

(52) U.S. Cl.
CPC .............. *A61K 31/137* (2013.01); *A61K 31/24* (2013.01)

(58) Field of Classification Search
CPC ..................... A61K 2300/00; A61K 31/1337; A61K 31/24
See application file for complete search history.

(56) References Cited

U.S. PATENT DOCUMENTS

| | | | |
|---|---|---|---|
| 3,832,460 A | 8/1974 | Kosti | |
| 4,279,901 A | 7/1981 | Kudla | |
| 4,877,781 A | 10/1989 | LaHaye et al. | |
| 4,952,560 A | 8/1990 | Kigasawa et al. | |
| 5,234,957 A | 8/1993 | Mantelle | |
| 5,332,576 A | 7/1994 | Mantelle | |
| 5,446,070 A | 8/1995 | Mantelle | |
| 5,624,676 A * | 4/1997 | Mackey et al. | 424/414 |
| 5,750,137 A | 5/1998 | Taskovich et al. | |
| 5,785,991 A | 7/1998 | Burkoth et al. | |
| 5,843,468 A | 12/1998 | Burkoth et al. | |
| 6,103,266 A | 8/2000 | Tapolsky et al. | |
| 6,214,318 B1 | 4/2001 | Osipow et al. | |
| 6,495,602 B1 | 12/2002 | Bhagwat et al. | |
| 6,582,724 B2 | 6/2003 | Hsu et al. | |
| 2002/0034455 A1 | 3/2002 | Lapidus | |
| 2002/0192273 A1 | 12/2002 | Buseman et al. | |
| 2003/0054017 A1 | 3/2003 | Castillo | |
| 2003/0104041 A1 | 6/2003 | Hsu et al. | |
| 2003/0161870 A1 | 8/2003 | Hsu et al. | |
| 2004/0037888 A1 | 2/2004 | Blanco | |
| 2004/0101557 A1 | 5/2004 | Gibson et al. | |

FOREIGN PATENT DOCUMENTS

JP    10-218780    8/1998

OTHER PUBLICATIONS

Federal Register, Special Edition, Code of Federal Regulations, Apr. 1, 2003, pp. 261:266.

* cited by examiner

*Primary Examiner* — Kyle Purdy
(74) *Attorney, Agent, or Firm* — Jeffrey M. Gold; Maureen P. O'Brien; Paula K. Davis

(57) ABSTRACT

The invention provides an oil-in-water emulsion useful in the treatment of anorectal disorders comprising a local anesthetic, vasoconstrictor, glycerin and water, and method of preparation of the emulsion and a method for treating hemorrhoids using the composition of the invention.

2 Claims, No Drawings

COMPOSITION AND METHOD FOR TREATING HEMORRHOIDS AND/OR ANORECTAL DISORDERS

CROSS-REFERENCE TO RELATED APPLICATIONS

This is a continuation application from U.S. application Ser. No. 12/614,084, which was filed on Nov. 6, 2009, which was a divisional application of U.S. application Ser. No. 10/884,454, which was filed on Jul. 2, 2004, now abandoned.

BACKGROUND OF THE INVENTION

1. Field of the Invention

The present invention is directed to an oil-in-water emulsion composition useful in the treatment of anorectal disorders such as hemorrhoids and use of the composition in the treatment of anorectal disorders such as hemorrhoids.

2. Description of Related Art

Hemorrhoids, a common ailment suffered by as many as nine out of ten Americans at some point in their lives, are swollen varicose veins in the mucous membrane inside or just outside the rectum. Hemorrhoids can be caused by constipation and the straining associated therewith as the excessive pressure involved can cause a fold of the membranous rectal lining to slip down, resulting in a pinching of the veins and subsequent irritation. Other causes may include diseases of the digestive tract resulting in an infection and diseases which obstruct blood flow, putting increased pressure on the hemorrhoidal veins. For example, pregnant women are prone to suffer hemorrhoids because of the pressure on the veins in the abdomen.

Hemorrhoidal symptoms can range from no noticeable symptoms to itching and mild discomfort to pain and/or bleeding. Once formed, the hemorrhoidal condition typically worsens over time, hence prompt treatment is desirable even in mild cases with few or no noticeable symptoms.

Treatment methods for hemorrhoids include soothing by immersion in a warm bath, application of ointments, gels and suppositories and surgery to curtail bleeding and to remove varicose veins. A single method of treatment or combination of treatment methods may be employed.

A number of patents and patent applications disclose and claim hemorrhoidal treatments. For example, U.S. patent application publication number 20040037888 discloses a gel preparation comprising a cellulose gelling agent, propylene glycol, and active ingredients. The water based system facilitates solublization of active ingredients but lacks the desirable tactile feeling of a cream and most likely the endurance at the site of treatment of a cream.

Related U.S. Pat. Nos. 5,234,957, 5,332,576 and 5,446,070 teach a composition comprising a polysaccharide bioadhesive carrier that is preferably water free. Active ingredients are dissolved in a solvent other than water. While this may facilitate preparation of the composition, the absence of water may impact the delivery of the active ingredient to body tissues. Evidence for this is found in U.S. Pat. No. 5,234,957 which teaches the use of concentrations of anesthetic actives substantially higher than approved FDA dosage amounts.

U.S. Pat. No. 6,582,724 discloses a composition which includes a hydroxide releasing agent such that the pH of the composition is pH 8.0 to pH 13. Such an alkaline pH would impact the stability of many active agents and preservation of the integrity of the composition over time would require special efforts.

U.S. patent application publication number 20020192273 discloses an adhesive patch for application of a therapeutic formulation for the treatment of hemorrhoids. Not only is a patch substrate required but also a pressure sensitive adhesive. Self application of such a patch to affected hemorrhoidal tissue may be fraught with some difficulty. Accomplishing adhesion at the desired location and/or discomfort in removing a patch adhered to hemorrhoidal tissue are exemplary of these difficulties.

U.S. patent application publication number 20030054017 claims a general method for application of a topical anesthetic to the skin. The method includes incorporating an anesthetic in a lipophilic base into a volatile solvent such as alcohol which will evaporate upon application to the skin. The disclosed composition is best suited for anesthetics which are preferentially soluble in non-polar/non-aqueous medium.

Many commercial preparations are available on the market for treatment of hemorrhoids. Many of these products are cream based preparations. Cream based compositions have the desirable properties of good tactile sensation and persistence on the area of treatment for a period of time. However, known cream based preparations typically suffer the significant deficiency of not dissolving many topical anesthetic agents and/or vasoconstrictors which are desirable active agents. While such agents may be physically dispersed in a cream, homogenous distribution as well as delivery to affected tissues may be problematic.

Hence, there remains a need for a cream type hemorrhoidal treatment with improved compatibility with dispersion and delivery of water soluble active agents.

SUMMARY OF THE INVENTION

The invention provides a pharmaceutical composition for treating hemorrhoids and/or anorectal disorders comprising an effective amount of a topical anesthetic, an effective amount of a vasoconstrictor, glycerin and water. The pharmaceutical composition is an oil-in-water emulsion and the topical anesthetic and the vasoconstrictor are solubilized in the water portion of the oil-in-water emulsion. The ratio of the glycerin amount by weight to the sum of the glycerin amount and water amount by weight in one embodiment is about 20% to about 45%. Further, the sum of the glycerin amount and water amount in one embodiment is at least 50% w/w of the pharmaceutical composition.

Vasoconstrictors useful in the practice of the invention include, but are not limited to, at least one of phenylephrine hydrochloride, ephedrine sulphate, epinephrine, epinephrine hydrochloride and tetrahydrozoline HCl. Anesthetics useful in the practice of the invention include, but are not limited to, at least one of benzocaine, benzyl alcohol, dibucaine, dibucaine HCl, pramoxine hydrochloride, tetrocaine, tetracaine HCl, dyclonine, and dyclonine HCl. The composition may further comprise at least one non-ionic emulsifier and/or about 12% w/w to about 18% w/w of a semisolid oleaginous protectant, and/or at least one antioxidant. In some embodiments a pH adjusting compound with buffering capacity may be added and the pH adjusted to a pH of less than about pH 6.

In one embodiment the invention provides a pharmaceutical composition for treating hemorrhoids and/or anorectal disorders in humans comprising pramoxine hydrochloride, phenylephrine hydrochloride, glycerin and water. The pharmaceutical composition is an oil-in-water emulsion, and the pramoxine hydrochloride and phenylephrine hydrochloride are solubilized in the water portion of the oil-in-water emulsion. The ratio of the glycerin amount by weight to the sum of the glycerin amount and water amount by weight is about 20% to about 45%. Further, the sum of the glycerin amount and water amount is at least 50% w/w of the pharmaceutical composition.

The composition may further comprise at least one non-ionic emulsifier, and/or about 12% w/w to about 18% w/w of a semisolid oleaginous protectant, and/or at least one antioxidant. A pH adjusting compound with buffering capacity may be added and the pH adjusted to a pH of less than about pH 6.

In another embodiment the invention provides a pharmaceutical composition for healing hemorrhoids and/or anorectal disorders in humans comprising about 0.5% w/w to about 3.0% w/w pramoxine hydrochloride, about 0.1% w/w to about 1.0% w/w phenylephrine hydrochloride, glycerin, water, about 0.1% w/w to about 0.3% w/w sodium benzoate, about 12% w/w to about 18% w/w petrolatum, about 0.2% w/w Tenox™, about 0.5% w/w mixed tocopherols, citric acid and at least one non-ionic emulsifier. The pharmaceutical composition is an oil-in-water emulsion, and the pramoxine HCl and phenylephrine HCl are solubilized in the water portion of the oil-in-water emulsion. The ratio of the glycerin amount by weight to the sum of the glycerin amount and water amount by weight is about 20% to about 45%, and the sum of the glycerin amount and water amount is at least 50% w/w of the pharmaceutical composition. The composition may further comprise about 0.1% w/w to about 2.0% w/w carboxymethylcellulose and about 0.01% w/w to about 1.0% w/w xanthan gum.

The invention further provides a method of preparing a composition for treating hemorrhoids and/or anorectal disorders in humans comprising preparing an oil-in-water emulsion comprising a topical anesthetic, a vasoconstrictor, glycerin and water wherein the topical anesthetic and the vasoconstrictor are solubilized in the water portion of the oil-in-water emulsion. The ratio of the glycerin amount to the sum of the glycerin amount and the water amount by weight is about 20% to about 45%, and the sum of the glycerin amount and the water amount is at least 50% w/w of the pharmaceutical composition.

The invention further provides a method of treatment of hemorrhoids and/or anorectal disorders in humans comprising administering to the anorectal region a safe and effective amount of the pharmaceutical composition of the invention disclosed herein.

DETAILED DESCRIPTION OF THE INVENTION

The invention provides an anesthetic cream composition which is an oil-in-water emulsion comprising a local anesthetic, a vasoconstrictor, glycerin and water. The inventors have discovered that certain ratios of glycerin and water facilitate not only the dispersion of water soluble local anesthetics and/or vasoconstrictors in the composition but also promote absorption into human body tissue. The cream of the invention has improved prolonged anesthesia particularly as compared to a typical gel preparation, other creams and ointments.

The cream of the invention may be formulated with petrolatum and an emulsification system, both of which may promote good rub-in properties and foster long-term stability under storage conditions. Further, the composition may include one or more antioxidants and/or be adjusted to an acidic pH using a composition that has buffering capacity.

The invention also provides a method for treating hemorrhoids and a method of preparation of the composition of the invention.

As used herein, "hemorrhoids" mean swollen varicose veins in the mucous membrane inside or just outside the rectum. The composition and methods of the invention may be used to treat diseases of the anorectum which manifest one or more symptoms of itching, discomfort, pain and bleeding. Accordingly, references to use of the composition and/or methods of the invention for treating hemorrhoids is equally applicable to diseases of the anorectum manifesting one or more symptoms in common with hemorrhoids.

The term "pharmaceutical active", "active pharmaceutical agent", "active agent" and "drug" as used herein should be considered to have the same meaning.

The terms "effective amount" or "therapeutically effective amount" of an active agent as provided herein is defined as an amount of the agent at least sufficient to provide the desired therapeutic effect.

The term "glycerin ratio" means the ratio of the weight of glycerin to the weight of glycerin plus the weight of water in the composition. Preferably this ratio is expressed as a percent.

The term "w/w", unless otherwise indicated, means weight of a given component or specified combination of components to total weight of the composition expressed as a percentage.

A designation that a substance is a solid, semisolid, liquid or gas should be taken to mean the physical state of the substance in the temperature range of about 20° C. to about 40° C.

A "vasoconstrictor" means a substance or agent that promotes the constriction of blood vessels in hemorrhoidal tissue (i.e. shrinks the hemorrhoidal tissue).

An "anesthetic" means a substance that is capable of producing a complete or partial loss of feeling.

As used herein, the term "treat" or "treating" or "treatment" means to provide relief of one or more of the symptoms associated with hemorrhoids. The relief may be provided by ameliorating one or more symptoms, reducing the hemorrhoid, and/or healing affected tissues, for example. Accordingly, the treatment of hemorrhoids can include the following: constriction of the blood vessels of the hemorrhoidal tissue and/or providing relief from the discomfort or pain from the burning, itching, swelling, irritation, soreness and/or inflammation of hemorrhoidal tissue.

The term "petrolatum" refers to petroleum jelly, which is a mixture of the softer members of the paraffin or methane series' of hydrocarbons, obtained from petroleum as an intermediate product in the distillation. Petrolatum is typically perceived as soothing when applied to the human skin.

Anesthetics suitable for use in the practice of the invention and suitable respective ranges of their amounts include, but are not limited to, benzocaine (about 5% to about 20% by weight, benzyl alcohol (about 1% to about 4% by weight), dibucaine and dibucaine HCl (about 0.25% to about 1% by weight); lidocaine and lidocaine HCl (about 0.5% to about 5% by weight); pramoxine hydrochloride (about 0.5 to about 1% by weight), tetracaine and tetracaine HCl (about 0.5% to about 1% by weight) and dyclonine and dyclonine HCl (about 0.5% to about 1.0% by weight) or mixtures thereof.

Use of pramoxine HCl as the anesthetic has several advantages. It is a long-acting surface anesthetic that fosters the relief of pain without the loss of the touch sensation (e.g.

without numbing). Further, pramoxine HCl is water soluble and has a low toxicity profile.

Vasoconstrictors suitable for use in the invention include, but are not limited to, phenylephrine hydrochloride, ephedrine sulphate, epinephrine, epinephrine hydrochloride and tetrahydrozoline HCl or mixtures thereof. In the embodiments in which phenylephrine HCl is the vasoconstrictor, the phenylephrine hydrochloride is used in an amount up to about 0.35% w/w of the total composition, more preferably about 0.1 to about 0.3%, and most preferably about 0.25%.

Glycerin (glycerol) is used in the practice of the invention in an amount of about 10% w/w to about 45% w/w. Further, the sum of the glycerin content and water content should be at least 50% w/w of the composition and the ratio of the glycerin content to the sum of the glycerin and the total water content ranges from about 20% to about 45%. Commercially available 96% glycerin 4% water may be used in the practice of the invention, however any water contained in the commercial glycerin product should be included in the determination of total water in the composition. Likewise glycerin amounts are based on actual amount of the chemical entity glycerin.

The inventors believe, without wishing to be bound to theory, that the glycerin and water amounts and amount of glycerin to the total amount glycerin and water (e.g. the glycerin ratio) are important factors in imparting some of the desired features of the invention. Glycerin alone can have a dehydrating effect which would not only potentially have the undesirable property of dehydrating the affected area but also may cause an uncomfortable sensation. However, glycerin in combination with suitable amounts of water has the desired feature of providing hydration to afflicted areas. As the preferred anesthetics and vasoconstrictors are water soluble, the water glycerol combination also facilitates penetration of the active agents into the afflicted area. Both the amounts of glycerin and water, as well as their relative proportions, are believed to be important to optimize the humectant properties of glycerin, facilitate the penetration of the active ingredients into the afflicted area, and facilitate hydration of the tissues. Hydration is believed to facilitate relief of itching, discomfort and pain. Hydration of the afflicted epithelial tissue is particularly important in the anorectal area since the rectal area is particularly devoid of water in comparison to other body cavities such as the buccal or vaginal cavity. Further improved penetration of the active agents in the afflicted areas is believed to provide improved anesthesia.

In one embodiment pramoxine HCl and phenylephrine HCl are the anesthesia and vasoconstrictor, respectively, in an oil-in-water emulsion. Glycerin is preferably present at a level, and at a ratio to the total formula quantity of glycerin and water to optimally promote the hydration of irritated epithelial tissue with the water phase of the oil-in-water emulsion. This facilitates delivery of the pramoxine HCl and phenylephrine HCl which are dissolved in the water to afflicted tissue. Preferably the amount of water is sufficient to fully solubilize the pramoxine HCl and phenylephrine HCl. Full solubilization presents the pharmaceutical actives as molecular species in a water medium. If the pharmaceutical actives are suspended in an oleaginous substance (e.g. not solubilized), the pharmaceutical actives are likely to be dispersed as aggregates of molecules.

Pramoxine HCl provides a long-acting surface anesthesia fostering the relief of pain without the loss of the touch sensation (e.g. a numbing feeling). The combination of pramoxine HCl with the vasoconstrictor phenylephrine HCl is believed to prolong the residence time of the pramoxine HCl at the inflamed/irritated tissue site, thus prolonging the anesthetic effect over a composition containing pramoxine HCl alone.

The composition of the invention may contain one or more antioxidants, preferably antioxidants that scavenge free radical oxygen species. Exemplary antioxidants include about 0.2% w/w Tenox-2™ (i.e. a mixture of butylated hydroxy anisol (BHA) and propyl gallate dissolved in propylene glycol) and mixed tocopherols at about 0.5% w/w. As many active agents such as pramoxine HCl and phenylepherine HCl, for example, are susceptible to oxidation by free radical species, it is desirable in some embodiments to use at least two antioxidants to provide enhanced protection against a range of oxidizing agents.

Other antioxidants that may be used include BHT (butylated hydroxy toluene), botanical extract antioxidants, flavinoid antioxidants, sodium ascorbate sodium metabisulphite. The antioxidants promote the chemical stability of active ingredients such as pramoxine HCl and phenylephrine HCl by protecting against oxidation by free radical oxygen species.

An organic acid may be used to adjust in the pH preferably to an acidic range below about pH 6 and more preferably a pH range of about 3.5 to about 4.2. Citric acid at a level of about 0.1% w/w to about 0.3% is exemplary of a suitable acid. The acid not only maintains a pH range that is optimal for the active components of the composition of the invention but also may serve to buffer the composition from alkali insult if the composition is put into commercial packaging. Other suitable organic acids include, but are not limited to, maleic acid, succinic acid and other weak organic acids. Phosphoric acid is also suitable for use in adjusting the pH and providing buffer capacity.

It is believed that the use of at least one antioxidant or at least one compound that adjusts the pH to acidic range and has a buffering capacity or both facilitates shelf-life stability by providing an optimum pH for stability of active ingredients and scavenging of free radicals which may promote degradation. The buffering capacity provides the capacity for neutralizing any alkali specie that might be introduced in the manufacturing process or from packaging. In some embodiments at least two antioxidants are used.

In an embodiment in which pramoxine HCl and phenylephrine HCl are the anesthetic and vasoconstrictor, respectively, it is preferable to maintain the pH below about pH 6.0 and more preferable to maintain the pH below about pH 4. The low pH is beneficial for reducing, for example, potential degradation of phenylephrine. Maintaining the pH in the preferred range may be accomplished by including, for example, citric acid in the composition. An acidic environment provides the additional benefit of anti-microbial action in addition to facilitating stability under storage conditions.

In one embodiment the oil phase contains about 12% w/w to about 18% w/w of a semisolid oleaginous protectant ingredient such as, for example, petrolatum. Petrolatum is believed to promote good rub-in properties and accordingly enhance delivery of the active agents. Other materials suitable for use in the oil phase include, but are not limited to, mineral oil, paraffin, white wax, coca butter, shea butter. The oil phase may comprise a single type of oil or semi-solid oleaginous product or mixtures thereof. Further, a given oil or semisolid oleaginous product may contain a mixture of chemically similar chemical species.

Suitable emulsifiers for low pH (e.g. acidic) embodiments of the composition are non-ionic emulsifiers which can tolerate a low pH. Suitable emulsifiers include, but are not limited to, esters and ethers of fatty acids and esters and ethers of fatty alcohols and sorbitan esters including ethoxylates and non-ethoxylates and mixtures thereof. Typical compounds used as anionic emulsifiers do not function as emulsifiers at low pH and some cationic emulsifiers may be irritating when left on the epithelial tissues for an extended period of time.

Typically a mixture of ethoxylated and non-ethoxylated emulsifiers are used. In some embodiments, for example in emulsions containing greater than 10% of an oleaginous semi-solid such as petrolatum, it is desirable to include an ethoxylated fatty alcohol, that is a solid at room temperature and at least one or more additional emulsifiers with viscosity building attributes such as, for example, cetyl alcohol and/or stearyl alcohol. A solid ethoxylated fatty alcohol is believed to promote stability at temperatures around 40° C., (e.g., may, for example, prevent cheesy appearance upon storage at 40° C.).

In one embodiment of the cream of the invention comprising pramoxine HCl, phenylephrine HCl, glycerin, water, sodium benzoate, about 12% to about 18% semi-solid petrolatum, a non-ionic emulsifier which is a solid at room temperature, about 0.1% to about 0.3% w/w of citric acid and the antioxidants Tenox-2 (about 0.2% w/w) and mixed tocopherols (about 0.5% w/w), exhibited superior physical/chemical stability in shelf life testing. In a cream containing pramoxine/phenylephrine which contained no pH buffers and no antioxidants, the pramoxine degradant n-butoxyphenol was observed upon storage. This degradant was not observed upon storage of the compound of the composition of the invention.

The composition of the invention may include one or more preservatives such as, but not limited to, methylparaben, propylparaben, sodium benzoate and phenoxyethanol, hydroxybenzoates, imidazole urea. In some embodiments at least two or more preservatives may be used, one of which preferentially dissolves in the water phase of the oil-in-water emulsion and another of which that preferentially dissolves in the oil portion of the active water emulsion. For example, the combination of methylparaben which is water soluble and propylparaben which is oil soluble may be used in the practice of the invention. Further benzyl alcohol in amounts up to about 1% w/w may be used as an auxiliary preservative.

The composition of the invention may also include chelating agents such as, for example, disodium edetate.

The composition of the invention may further include emollients and anti-irritants such as, for example including but not limited to, aloe vera oil, Vitamin E acetate, D-panthenol, green tea extract, heat-shock proteins and phytosterols.

In one embodiment carboxymethylcellulose and/or xanthan gum may be included in the composition of the invention to modify texture, promote a smooth consistency over time and storage conditions, mitigate against graininess and/or promote a smooth and shiny appearance. The composition of the invention is an oil-in-water emulsion not a gel. Accordingly amounts of carboxymethylcellulose and xanthan gum should be sufficient to impart a smooth appearance to the cream of the invention but at insufficient levels to form a gel. Carboxymethylcellulose may be used in an amount of about 0.1% w/w to about 2.0% w/w and more preferably about 0.25% w/w to about 2.0% w/w. Xanthan gum may be used in an amount of about 0.01% to about 1.0%. Aqualon 7MF™ is exemplary of a Carboxymethylcellulose suitable for use in the practice of the invention. Rodigel 80™ from R. T. Vanderbildt is exemplary of a suitable xanthan gum.

Optionally, menthol may be included in composition of the invention as a sensory efficacy cue to provide a user of the composition with an immediate anti-pruritic (e.g. anti-itch) effect and a decided cooling sensation. Typically about 0.01% to about 1.0% w/w menthol may be included.

Optionally, fragrances known to those in the pharmaceutical industry may be included.

The composition of the invention is intended for topical application to the affected tissue. The composition may be applied intrarectally and/or to the anorectal region. The typical method of use is application one to four times daily of an aliquot of the composition to the afflicted tissue with gentle rubbing.

The composition of the invention is typically prepared by combining the oil component(s) and the emulsifier(s) and then combining the oil/emulsifier mixture with the water and the glycerin components. Preferably if carboxymethylcellulose and/or xanthan gum are used, they are dispersed in the glycerin and hydrated with water prior to combination of the water and glycerin (e.g. water/glycerin component) with the oil/emulsifier component. The oil emulsifier component and glycerin/water component should be combined with vigorous stirring. In some embodiments it is desirable that the combination process be conducted at elevated temperatures. In an exemplary embodiment the combining process was conducted at about 70-75° C. The amount of heating will vary depending on the oils used and should be sufficient to promote formation of the emulsion but not so high as to promote degradation of components.

Components not specifically mentioned may be added at any one of a variety of points in the process as one skilled in the art will appreciate. Typically oil soluble components not susceptible to heat degradation up to about 100° C. were dissolved in the oil/emulsifier mixture prior to mixing with the glycerin/water dispersion and water soluble components that have degradation at temperature below about 100° C., were combined in the emulsion mixture after combination of the oil emulsifier and water/glycerin components and cooling of the emulsion to near ambient temperature typically about 50° C. Further, it is preferable in some embodiments to add salts and acids after the emulsion is formed as addition prior to forming the emulsion may adversely impact emulsion formation in some cases.

EXAMPLE 1 ANORECTAL CREAM

The following example describes a pharmaceutical composition, which is exemplary of the oil-in-water emulsion for treating hemorrhoids and/or anorectal disorders of the present invention.

|  | % W/W |
|---|---|
| ACTIVE INGREDIENTS | |
| Pramoxine HCl, USP | 1.00 |
| Phenylephrine HCl, USP | 0.250 |
| Glycerin, USP | 14.4 |
| White Petrolatum, USP | 15.0 |
| INACTIVE INGREDIENTS | |
| Methylparaben, NF | 0.200 |
| Propylparaben, NF | 0.100 |
| Sodium Benzoate, NF | 0.200 |

-continued

|  | % W/W |
|---|---|
| Disodium Edetate USP | 0.0500 |
| Mixed Tocopherols Antioxidant | 0.500 |
| Propyl Gallate and BHA in Propylene Glycol | 0.200 |
| Steareth-20 | 1.00 |
| Steareth-2 | 1.00 |
| Glyceryl Monostearate and Laureth-23 (70/30) | 3.00 |
| Stearyl Alcohol, NF | 5.00 |
| Cetyl Alcohol, NF | 5.00 |
| Sodium Carboxymethylcellulose, USP | 0.250 |
| Xanthan, NF | 0.100 |
| Citric Acid, USP | 0.200 |
| Aloe Vera Oil | 0.100 |
| Vitamin E Acetate, USP | 0.100 |
| D-Panthenol, USP | 1.00 |
| Purified Water, USP | 51.35 |

The composition of Example 1 was prepared by melting the oil component (i.e. white petrolatum for this example) and combining the melted oil with the emulsifiers, emollients, antioxidants and preservatives (i.e. emulsifiers: steareth-20, steareth-2, glyceryl monosterate and laureth-23 (70/30) stearyl alcohol and cetyl alcohol; emollients: Vitamin E, aloe vera oil; antioxidants: Tenox 2™ and mixed tocopherols; and preservatives: methyl paraben and propylparaben). The sodium carboxymethylcellulose and xanthan gum were dispersed in the glycerin and then hydrated by mixing the glycerin dispersion with water. The disodium edetate was added to the glycerin/water dispersion.

The glycerin/water dispersion was combined with oil/emulsifier mixture with vigorous mixing and with heating to about 70-75° C. Upon thorough mixing the composition was cooled to about 50° C. and the pharmaceutical actives, other heat labile components, salts and acids (e.g. sodium benzoate, panthenol, and citric acid) were added.

Physical characteristics of the composition of Example 1 were measured by means known to those skilled in the art. The measured physical characteristics of the composition of Example 1 include Specific Gravity: 0.983; pH: 3.93; and Viscosity: 44,980 cps at the time of manufacture, 159,000 cps three days after manufacture and 179,000 cps seven days after manufacture.

Although the foregoing invention has been described in some detail by way of illustration and examples for purposes of clarity and understanding, it will be obvious that certain changes and modifications may be practical within the scope of the appended claims. Modifications of the above-described modes of practicing the invention that are obvious to persons of skill in the art are intended to be included in the scope of the following claims.

What is claimed is:

1. A pharmaceutical composition consisting of 1.00% w/w pramoxine hydrochloride, 0.250% w/w phenylephrine hydrochloride, 15.0% w/w white petrolatum, 14.4% w/w glycerin, 1.00% w/w steareth-20, 1.00% w/w steareth-2, 3.00% w/w glyceryl monostearate and laureth-23 70/30, 5.00% w/w stearyl alcohol, 5.00% w/w cetyl alcohol, 0.200% w/w methylparaben, 0.100% w/w propylparaben, 0.200% w/w sodium benzoate, 0.0500% w/w disodium edetate, 0.500% w/w mixed tocopherols, 0.200% w/w propyl gallate and BHA in propylene glycol, 0.250% w/w sodium carboxymethylcellulose, 0.100% w/w xanthan, 0.200% w/w citric acid, 0.100% w/w aloe vera oil, 0.100% w/w vitamin E acetate, 1.00% w/w D-panthenol, and 51.35% w/w water; wherein the pharmaceutical composition is an oil-in-water emulsion and the oil-in-water emulsion is a cream, wherein the pramoxine hydrochloride and phenylephrine hydrochloride are solubilized in the water portion of the oil-in-water emulsion, wherein the at least one non-ionic emulsifier includes an ethoxylated fatty alcohol that is a solid at room temperature, wherein the ratio of the glycerin amount by weight to the sum of the glycerin amount and water by weight is about 20% to about 45%, wherein the pH range of the composition is about 3.5 to about 4.2, and wherein the composition provides hydration to hemorrhoid and/or anorectal tissue.

2. A method of treating hemorrhoids and/or anorectal disorders in humans comprising administering to the anorectal region a safe and effective amount of a pharmaceutical composition, the pharmaceutical composition consisting of 1.00% w/w pramoxine hydrochloride, 0.250% w/w phenylephrine hydrochloride, 15.0% w/w white petrolatum, 14.4% w/w glycerin, 1.00% w/w steareth-20, 1.00% w/w steareth-2, 3.00% w/w glyceryl monostearate and laureth-23 70/30, 5.00% w/w stearyl alcohol, 5.00% w/w cetyl alcohol, 0.200% w/w methylparaben, 0.100% w/w propylparaben, 0.200% w/w sodium benzoate, 0.0500% w/w disodium edetate, 0.500% w/w mixed tocopherols, 0.200% w/w propyl gallate and BHA in propylene glycol, 0.250% w/w sodium carboxymethylcellulose, 0.100% w/w xanthan, 0.200% w/w citric acid, 0.100% w/w aloe vera oil, 0.100% w/w vitamin E acetate, 1.00% w/w D-panthenol, and 51.35% w/w water;
wherein the pharmaceutical composition is an oil-in-water emulsion and the oil-in-water emulsion is a cream, wherein the pramoxine hydrochloride and phenylephrine hydrochloride are solubilized in the water portion of the oil-in-water emulsion, wherein the at least one non-ionic emulsifier includes an ethoxylated fatty alcohol that is a solid at room temperature, wherein the ratio of the glycerin amount by weight to the sum of the glycerin amount and water by weight is about 20% to about 45%, wherein the pH range of the composition is about 3.5 to about 4.2, and wherein the composition provides hydration to hemorrhoid and/or anorectal tissue.

* * * * *